United States Patent [19]
Besecker et al.

[11] Patent Number: 4,900,853
[45] Date of Patent: Feb. 13, 1990

[54] SALTS AND RESINOIDS OF 1:4 ORGANOARSONATE MOLYBDENUM POLYOXOANIONS AND PROCESS OF MAKING

[75] Inventors: Charles J. Besecker, Cleveland; William A. Marritt, Cleveland Heights, both of Ohio

[73] Assignee: The Standard Oil Company, Cleveland, Ohio

[21] Appl. No.: 81,842

[22] Filed: Aug. 5, 1987

[51] Int. Cl.$^4$ .................. C07F 7/00; C08G 79/00
[52] U.S. Cl. ................................ 556/30; 556/64
[58] Field of Search ...................... 556/30, 56, 64

[56] References Cited

U.S. PATENT DOCUMENTS

| | | | |
|---|---|---|---|
| 3,341,477 | 9/1967 | Washburn et al. | 260/2 |
| 3,346,604 | 10/1967 | Leathwhite et al. | 260/429 |
| 4,237,061 | 12/1980 | Johnson | 260/429.3 |
| 4,374,242 | 2/1983 | Dines et al. | 528/395 |

OTHER PUBLICATIONS

W. Kwak, L. M. Rajkovic, J. K. Stalick, M. T. Pope and C. O. Quicksall "Synthesis and Structure of Hexamolybdobis (organoarsonates)", Inorg. Chem., 15, 2778 (1976).

M. Filowitz and W. G. Klemperer, "$^{17}$O Nuclear Magnetic Resonance Structure Determinations of As$_2$Mo$_6$O$_{26}^{6-}$ and (PhAs)$_2$Mo$_6$O$_{24}^{4-}$" J.C.S. Chem. Comm. 233–234 (1976).

M. Filowitz, R. K. C. Ho, W. G. Klemperer and W. Shum, "$^{17}$O Nuclear Magnetic Resonance Spectroscopy of Polyoxometalates. 1. Sensitivity and Resolution" Inorganic Chemistry, 18, pp. 93–103 (1979).

Primary Examiner—Glenn Caldarola
Attorney, Agent, or Firm—Larry W. Evans; Joseph G. Curatolo; Teresan W. Gilbert

[57] ABSTRACT

Tetraalkylammonium salts of 1:4 organoarsonate molybdenum polyoxoanions and resinoid products thereof. The salts have the formula

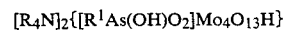

where R is an alkyl group having from one to about 18 carbon atoms and R$^1$ is an aryl group having the formula

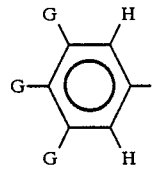

where G is selected from the group consisting of —NH$_2$, —NH(CH$_3$), —N(CH$_3$)$_2$, —OH, —OCH$_3$ and —H and at least one G is —NH$_2$ to form 3-, 4-, 3,4-, 3,5- or 3,4,5-substituted aryl-arsonic acids. The resinoids comprise from about 7 to 17 parts by weight of the salt and from about 1 to 3 parts by weight of a dicarboxylic acid halide having the formula

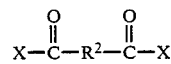

where R$^2$ is selected from the group consisting of all organic radicals and X is Cl or Br. Processes for the preparation of the salts and resinoids are provided as is a method for the treatment of steel surfaces with the resinoids.

6 Claims, No Drawings

SALTS AND RESINOIDS OF 1:4 ORGANOARSONATE MOLYBDENUM POLYOXOANIONS AND PROCESS OF MAKING

TECHNICAL FIELD

The present invention provides organoarsonate molybdenum polyoxoanions having a molecular ratio of arsenic to molybdenum of 1:4. Novel tetraalkylammonium salts of the anion and their preparation are also described. The salts can be reacted with dicarboxylic acid halides and form resinoids which can be readily utilized in a method to coat metal surfaces thereby affording a relatively simple method for protecting metal surfaces from corrosion.

BACKGROUND ART

The synthesis and structure of several water soluble organoarsonomolybdate salts having an arsenic:molybdenum ratio of 2:6 isolated from concentrated aqueous solutions acidified to pH range of 4-5 has been reported by Kwak, W.; Rajkovic, L. M.; Stalick, J. K.; Pope, M. T. and Quicksall, C. O., "Synthesis and Structure of Hexamolybdobis(organoarsonates)" Inorg. Chem., 15, 2778 (1976).

Preparation of 4:12 organoarsonate and 1:4 organoarsinate species by reacting phenylarsonic acid or dimethylarsinic acid, respectively, with a sodium molybdate solution and adjusting the pH with concentrated mineral acid is reported by Filowitz, M.; Ho, R. K. C.; Klemperer, W. G. and Shum, W. "$^{17}$O Nuclear Resonance Spectroscopy of Polyoxometalates. 1. Sensitivity and Resolution" Inorg. Chem., 18, 93 (1979).

U.S. Pat. No. 4,374,242 is directed toward layered organoarsenous, inorganic polymers which are prepared by reacting an organoarsenic acid with at least one tetravalent metal ion. Preferred metals include zirconium, titanium, uranium, cerium, lead and hafnium but not molybdenum. The polymers have utility as exchange resins and as carriers for the controlled release of biologically active organic compounds.

Insoluble organic quaternary ammonium complexes derived from heteropolyanionic acids such as phosphomolybdic, phosphotungstic, silicomolybdic and silicotungstic are described in U.S. Pat. No. 3,346,604. Although these complexes do not incorporate arsenic, they can be added to primer compositions as anti-corrosion agents.

Despite the synthesis of various organoarsonomolybdate anions and other heteropolyoxoanions the art has not disclosed tetraalkylammonium salts of 1:4 organoarsonate molybdate polyoxoanions or the reaction of salts thereof with dicarboxylic acid halides to form corrosion resistant coatings for metals.

DISCLOSURE OF THE INVENTION

It is therefore an object of the present invention to provide organoarsonate molybdenum polyoxoanions having a molecular ratio of arsenic to molybdenum of 1:4.

It is another object of the present invention to provide tetraalkylammonium salts of 1:4 organoarsonate molybdenum polyoxoanions having the formula

[R$_4$N]$_2${[R$^1$As(OH)O$_2$]Mo$_4$O$_{13}$H} where R is an alkyl group having from one to about 18 carbon atoms and R$^1$ is an aryl group having the formula

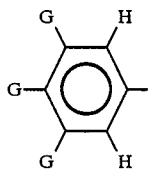

where G is selected from the group consisting of —NH$_2$, —NH(CH$_3$), —N(CH$_3$)$_2$, —OH, —OCH$_3$ and —H and at least one G is —NH$_2$ to form 3-, 4-, 3,4-, 3,5-, or 3,4,5-substituted arylarsonic acids.

It is a further object of the present invention to provide processes for the preparation of salts of tetraalkylammonium salts of 1:4 organoarsonate molybdenum polyoxoanions and resinoids thereof.

The process for the preparation of such salts comprises the steps of preparing an aqueous solution of an arylarsonic acid having the formula

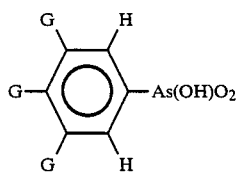

where G is selected from the group consisting of —NH$_2$, —NH(CH$_3$), —N(CH$_3$)$_2$, —OH, —OCH$_3$ and —H and at least one G is —NH$_2$, with an inorganic molybdenum compound selected from the group consisting of molybdenum oxide and molybdates of ammonium and the alkali metals, acidifying the solution to a pH of from about 3 to 5.5, forming a precipitate by adding to the solution a compound having the formula (R$_4$N)$^+$X$^-$ where R is an alkyl group having from one to about 18 carbon atoms and X is selected from the group consisting of inorganic and organic radicals that will not interfere with the salt forming reactions and, thereafter collecting the precipitate comprising acid salt.

It is yet another object of the present invention to provide resinoids comprising from about 7 to 17 parts by weight of a tetraalkylammonium salt having the formula

[R$_4$N]$_2${R$^1$As(OH)O$_2$]Mo$_4$O$_{13}$H} and from about 1 to 3 parts by weight of a dicarboxylic acid halide having the formula

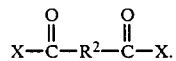

The process for the preparation of resinoids comprising the steps of preparing a first solution comprising a dicarboxylic acid halide having the formula

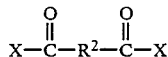

where $R^2$ is selected from the group consisting of all organic radicals and X is Cl or Br, preparing a second solution comprising a salt having the formula $[R_4N]_2\{[R^1As(OH)O_2]Mo_4O_{13}H\}$ as described hereinabove and a base having the formula

where R is selected from the group consisting of aliphatically saturated hydrocarbyls having from one to about 18 carbon atoms bonded to N through aliphatic carbons to form a mixture, mixing the first and second solution for at least about 1 hour at a temperature ranging from about 15° C. to 50° C., subsequently adding an anion exchange resin while stirring for about 12 hours to form a viscous layer of resinoid and, thereafter, precipitating the resinoid from the reaction components.

It is another object of the present invention to provide a method for treating steel surfaces to impart corrosion resistance which comprises the step of coating the surfaces with a resinoid of the present invention.

These and other objects, together with the advantages thereof over the prior art, which shall become apparent from the specification which follows, are accomplished by the invention as hereinafter described and claimed.

PREFERRED MODE FOR CARRYING OUT THE INVENTION

The salts of the present invention are prepared by the reaction of an organoarsonic compound with an inorganic molybdenum compound and then a precipitating cation. The organoarsonic compound is of the general formula

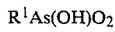

where $R^1$ is an aryl group having the formula

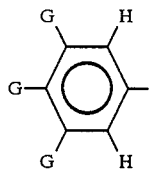

where G is selected from the group consisting of —NH$_2$, —NH(CH$_3$), —N(CH$_3$)$_2$, —OH, —OCH$_3$ and —H and at least one G is —NH$_2$ to form 3-, 4-, 3,4-, 3,5- or 3,4,5-substituted arylarsonic acids. It can be employed in the form of the free acid or any mono- or di-basic salt which is soluble in water or becomes soluble under the reaction conditions. A preferred free acid is 4-aminophenylarsonic acid.

The molybdenum source can be virtually any inorganic molybdenum oxide or oxo salt, providing the oxide or salt is soluble in water or becomes soluble under the reaction conditions. Common sources include molybdenum oxide, sodium molybdate and ammonium heptamolybdate which is preferred.

The precipitating cation, two of which are associated with the organoarsonomolybdate anion in the final product, is of the general formula $R_4N^+$, where R is an aliphatically saturated hydrocarbyl bonded to N through aliphatic carbons. R may contains from 1 to about 18 carbons with the minimum value dependent on the aqueous solubility of the corresponding organoarsonomolybdate salt. For a given substituted arylarsonic acid, R must contain sufficient carbons such that the corresponding organoarsonomolybdate anion is precipitated immediately and practically quantitatively upon addition of the quaternary ammonium salt. Typical minimum values for R are 2 or 3 with 4 being the preferred carbon number for the unbranched hydrocarbyl quaternary ammonium cation. The counterion associated with the precipitating cation can be any inorganic or organic anion which does not interfere with the principal reaction. Common counterions include fluoride, chloride, bromide, nitrate, hydrogensulfate, perchlorate, trifluoroacetate, trifluoromethanesulfonate, phenylsulfonate, tetrafluoroborate, hexafluorophosphate, hexafluoroantimonate and the like with bromide being preferred.

Preparation of the salt according to the process of the present invention is performed by the acidification of the arylarsonic acid or salt thereof and the molybdenum compound, in aqueous solution, with virtually any inorganic or organic acid, provided that the acid does not interfere with the principal reaction, for example, by causing reduction of the reactants. Typical acids include nitric, hydrochloric, sulfuric, phenylsulfonic and the like with sulfuric (6M) being preferred. The ratio of arylarsonic acid to molybdenum can range from about 1:1 to about 1:10 with 1:4 being preferred. The reaction is conducted between about 5° to 100° C. with 40° C. preferred with stirring for about 30 minutes to 3 hours.

The resulting solution is cooled to about 0° C. and the precipitating cation solution is added. A precipitate forms upon addition and the resulting slurry is stirred for a period of time of from about 1 to 16 hours while maintaining a temperature between about 0° C. and 20° C. and a pH of from about 3 to 5.5, with 4 being preferred by the addition of dilute acid as needed. After equilibration of the pH, the slurry is additionally stirred following which the solid product is filtered, washed and can be optionally recrystallized, all according to conventional procedure known to those skilled in the art.

The organoarsonate molybdenum salt can then be reacted with a dicarboxylic acid halide having the formula

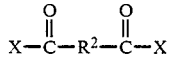

where $R^2$ is essentially any aliphatic or aromatic radical including, for instance, alkyl, aryl, acyl, alkaryl, aralkyl, alkoxy, aryloxy, ether, ester or other heterocycle, thio derivatives of the foregoing and the like, and X is Cl or Br. A preferred dicarboxylic acid halide is terephthaloyl chloride.

The salt and acid halide are combined in ratios of from about 7 to 17 parts salt to 1 to 3 parts acid halides on a weight percent basis in the presence of a solvent or solvent mixture selected on the basis of the solubility characteristics of each component. Suitable solvents include cyclohexane, propylene carbonate, dimethylacetamide and toluene.

To prepare the resinoids of the present invention three reactants are required. First is the tetraalkylammonium salt which has the formula $$[R_4N]_2\{R^1As(OH)O_2]Mo_4O_{12}\}$$

where R and $R^1$ are as defined hereinabove. The second component is the dicarboxylic acid halide monomer which has the formula $$\underset{X-\underset{\underset{O}{\|}}{C}-R^2-\underset{\underset{O}{\|}}{C}-X}{}$$

where $R^2$ and X are as defined hereinabove. The third component is a base, utilized to scavenge the hydrohalic acid liberated per mole of amide bond formation. The formula of the base is $$R^3{}_3N$$

where $R^3$ is an aliphatically saturated hydrocarbyl bonded to N through aliphatic carbons and having up to about 20 carbon atoms and preferably greater than 6 carbon atoms.

The resinoid is formed by preparing a first solution of the dicarboxylic acid halide, adding a second solution of the tetraalkylammonium salt and the foregoing base $R_3N$ to the first and mixing the two solutions together for a period of time ranging from about 30 minutes to 2 hours. Phase separation occurs providing an upper layer and a lower layer, the latter containing the resinoid. The best solvent system for preparation of the resinoid is a mixture tailored to the solubility characteristics of each of the monomers and where terephthaloyl chloride is selected, cyclohexane/propylene carbonate is preferred.

Subsequently, the reaction mixture is stirred for about 1 to 16 hours in the presence of an excess of strongly basic anion exchange resin (free base form), such as Amberlyst A21 presoaked in a dry solvent with a high affinity for water such as acetonitrile, THF or pyridine. The resin beads are then removed from the reaction mixture by suction filtration and extraction from the filtrate with cyclohexane. After removal of the resin beads from the filtrate, a clear, pale-yellow, viscous solution of the polymer in propylene carbonate is obtained. Precipitation with diethyl ether followed by drying in vacuo will produce a colorless air-stable solid which dissolves slowly in very polar organic solvents such as $CH_3CN$, $CH_3NO_2$, NMP and the like to yield colorless, extremely viscous solutions.

Composition of the resinoid comprises from about 7 to 17 parts by weight of the tetraalkylammonium salt of the present invention and from about 1 to 3 parts by weight of the foregoing dicarboxylic acid halide.

In the actual work reported hereinbelow, the preparation of a novel organoarsonate molybdenum salt according to the process of the present invention is set forth. Conventional techniques including washing, filtering and drying are also set forth although they do not provide any novelty to the process. A resinoid is thereafter prepared and employed as a coating on steel plates.

EXAMPLE NO. 1

General Procedures

Arsanilic acid (para) was purified by adding water to filtered hot ethanol solutions and removing the ethanol on a rotovap. Terephthaloyl chloride was recrystallized by cooling hot saturated cyclohexane solutions to $-30°$ C. The recrystallized material was stored in air tight containers sealed under nitrogen in order to prevent hydrolysis. Cyclohexane was refluxed and then distilled under argon over sodium benzophenone ketyl. Acetonitrile was distilled under nitrogen over $CaH_2$. Propylene carbonate was vacuum distilled. Diethyl ether was anhydrous grade and used only from freshly opened cans.

Preparation of
$[(n-C_4H_9)_4N]_2\{[4-H_2NC_6H_4As(OH)O_2]Mo_4O_{13}\}\cdot 3C_4H_8O_2$ A slurry of p-arsanilic acid (20.00 g, 0.092 moles) in 150 ml of water was added with stirring to a solution of ammonium heptamolybdate (65.00 g, 0.053 moles) in 300 ml of water. The resulting solution was warmed to 40° C. and acidified with 6M sulfuric acid to pH 4. At this point the solution was filtered through a fine porosity sintered glass frit and the filtrate cooled to 0° C. in an ice bath. A filtered solution of tetra-n-butylammonium bromide (71.0 g, 0.22 moles) in 150 ml of water was added slowly to the cooled, efficiently stirred arsonomolybdate solution. An off-white solid precipitated immediately. While continuing to stir the slurry, the pH was periodically adjusted to pH 4 using small additions of the dilute sulfuric acid over a period of 2 to 3 hours. After equilibration, the slurry was stirred for an additional 2 hours.

Recrystallization

The solid was collected by vacuum filtration, washed with several portions of cold water, dioxane and diethyl ether and dried with suction overnight. The solid was recrystallized by dissolving it in a minimal volume of propylene carbonate with stirring and gentle warming to 35° C. The resulting light green solution was gravity filtered. Dioxane ($C_4H_8O_2$) was added to the stirred filtrate to the point at which fine white crystals began to appear. Additional portions of dioxane were added to the point of incipient cloudiness, while stirring the slurry as it slowly cooled to ambient temperature over an approximately one hour period. The white crystals were collected by vacuum filtration and then washed with dioxane and diethyl ether. The product was dried in vacuo over $P_4O_{10}$ (yield 104.2 g, 72.6%).

Solvate Free Salt

The unrecrystallized product of Example No. 1 was also used to prepare a solvate free salt. To do so, a portion of the total collected solid (2–10 g) was dissolved in 20–50 ml of pyridine with warming and stirring. The solution was then gravity filtered through fluted Whatman #2 filter paper while still warm. Small white crystals deposited upon cooling of the filtrate to ambient temperature. The crystals were collected by suction filtration, washed with diethyl ether, and dried in vacuo over $P_4O_{10}$.

As noted hereinabove, the organoarsonomolybdate salts of this invention have demonstrated reactivity toward dicarboxylic acid chlorides in the presence of a trialkylamine base. The principal insoluble product of the reaction between the salt of Example No. 1 and terephthaloyl chloride is a resinoid, the preparation of which appears in Example No. 2. Steel surfaces which have been coated with solutions of this resinoid have been shown to be more corrosion resistant than untreated surfaces.

EXAMPLE NO. 2
Preparation of Resinoid

Inside a nitrogen filled glove bag, a solution of terephthaloyl chloride (0.897 g, 4.42 mmol) in cyclohexane (150 ml) was prepared in a 200 ml Schlenk flask. This solution was then transferred via cannula, under an argon atmosphere, to a rapidly stirred solution of the salt prepared in example No. 1 (10.0 g, 6.41 mmol) and trioctylamine (4.4 ml, 10 mmol) in propylene carbonate (50 ml). A small increase in solution viscosity was detected as the reaction proceeded. Stirring was continued for 30 minutes after the addition was completed. After phase separation, the upper cyclohexane layer was clear and colorless and the lower propylene carbonate layer was clear and pale yellow. Excess anion exchange resin (30 g, 1 mmol/g capacity, bead form, Amberlyst A21 obtained from Alfa, presoaked with 4×50 ml acetonitrile to remove most of the water) was added and the reaction mixture was then stirred overnight. During this time the solution viscosity of the polar layer was observed to increase dramatically. The resin beads were removed by suction filtration and the filtrate was extracted with 4×50 ml cyclohexane. Addition of excess ether to the extracted propylene carbonate layer resulted in precipitation of the product. After washing with ether, the resinoid product was collected by suction filtration and dried in vacuo. Dry weight obtained was 6.2 g.

In order to demonstrate the effectiveness of the resinoid as a corrosion resistance coating for steel a solution of the polymer in acetonitrile approximately 15 weight percent, was prepared and sonication was used to increase the dissolution rate. A requisite amount of N-methylpyrrolidone (NMP), approximately 15 weight percent, was added to the resulting solution to reduce the solution viscosity to a level acceptable for coating application.

Coatings were then applied to several carbon steel panels, sandblasted to remove all coatings and flattened on a magnetic chuck, using a wire wound roller. After drying under ambient conditions for about 15 minutes the panels were transferred to a forced circulating air oven preheated to 75° C. for 30 minutes. The oven temperature was raised to 125° C. and then maintained at this temperature for an additional 90 minutes. Finally, the oven temperature was raised to 160° C. and the panels were baked at this temperature for 90 minutes. After equilibration under ambient conditions, a second coat of polymer was applied and the thermal cure treatment was repeated.

After ambient equilibration, the panels were subjected to ASTM B 117 salt exposure testing in a standard salt-fog cabinet. The cabinet induced accelerated corrosion testing through exposure of the specimens to a salt-fog atmosphere. The panel was examined periodically and rated by comparison to published standards. The rating values range from 0 to 10, with a 0 rating indicative of all rust and a 10 rating indicative of no appreciable rust. The scale is logarithmic between the two extreme endpoints.

The treated panels were visually examined every 24 hours. Under salt-fog test conditions, visual evidence of corrosion was not detectable after 70 hours. An identically sandblasted panel, which had not been coated with the resinoid, yielded a test rating of about 5 after 24 hours of identical salt-fog exposure. An additional 24 hours of salt-fog exposure for the control panel resulted in maximal rusting corresponding to a rating of 10. For the treated panel, the onset of a gradual failure process occurred after continued salt-fog exposure beyond 70 hours.

The typical evidence for corrosive failure of conventional organic coatings, concentrically growing rust fronts emanating from pinholes and propagating by film delamination, was not observed at this point. Instead, the imperviousness of the original coating appeared to be reduced and a faint rust film was evident over extended sections of the panel. It is noteworthy that typical delaminative failure did not occur. The severity of the corrosion increased gradually with time and severe pitting eventually occurred after one week.

Based upon the foregoing exemplification, it can be seen that the present invention provides novel tetraalkylammonium salts of organoarsonate molybdenum polyoxoanions as well as a process for the preparation thereof and that such salts can be employed to prepare resinoids having utility as corrosion resistant coatings. It is to be understood that the examples reported herein have been provided to present results obtainable by practice of the disclosed invention. Inasmuch as a wide variety of reactants have been disclosed to prepare the salts and resinoids of this invention, we do not intend to limit our invention to the specific examples provided herein. Furthermore, the processes for preparing these salts and resinoids are believed by us to be operable with other reactants, solvents and conditions than those which have been exemplified herein. Thus, it should be evident that the determination of particular solvents, reactants and the like, as well as the amounts thereof, can be made without departing from the spirit of the invention herein disclosed and described, and that the scope of the invention shall include all modifications and variations that fall within the scope of the attached claims.

We claim:

1. Tetraalkylammonium salts of 1:4 organoarsonate molybdenum polyoxoanions, said salts having the formula $$[R_4N]_2\{[R^1As(OH)O_2]Mo_4O_{13}H\}$$

where R is an alkyl group having from one to about 18 carbon atoms and $R^1$ is an aryl group having the formula

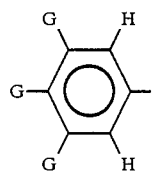

where G is selected from the group consisting of —$NH_2$, —$NH(CH_3)$, —$N(CH_3)_2$, —OH, —$OCH_3$ and —H and at least one G is —$NH_2$ to form 3-, 4-, 3,4-, 3,5- or 3,4,5-substituted arylarsonic acids.

2. A tetraalkylammonium salt, as set forth in claim 1, wherein R is n-$C_4H_9$ and G is —$NH_2$, —H and —H.

3. A process for the preparation of tetraalkylammonium salts of 1:4 organoarsonate molybdenum polyoxoanions comprising the steps of:
   preparing an aqueous solution of an arylarsonic acid having the formula

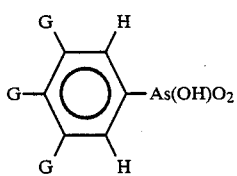

where G is selected from the group consisting of —NH$_2$, —NH(CH$_3$), —N(CH$_3$)$_2$, —OH, —OCH$_3$ and —H and at least one G is —NH$_2$, with an inorganic molybdenum compound selected from the group consisting of molybdenum oxide and molybdates of ammonium and the alkali metals;

acidifying said solution to a pH of from about 3 to 5.5;

forming a precipitate by adding to said solution a compound having the formula $$(R_4N)^+X^-$$

where R is an alkyl group having from one to about 18 carbon atoms and X is selected from the group consisting of inorganic and organic radicals that will not interfere with the salt forming reactions; and thereafter collecting the precipitate comprising acid salt.

4. A process, as set forth in claim 3, wherein G is —NH$_2$, —OH and —H, R is n-C$_4$H$_9$ and said molybdenum compound is ammonium molybdate.

5. A process, as set forth in claim 4, wherein said step of acidifying is conducted at a temperature ranging from about 5° C. to about 100° C.

6. A process, as set forth in claim 5, wherein said step of precipitating is conducted at a temperature ranging from about 0° C. to about 20° C. for a period of from about 1 to 16 hours.

* * * * *